United States Patent [19]

Berry et al.

[11] Patent Number: 4,597,885

[45] Date of Patent: Jul. 1, 1986

[54] ENCAPSULATED FOAMING BATH COMPOSITION

[75] Inventors: Ira R. Berry, Westfield; Dilip Shah, Parsippany; Lionel Borkan, New Vernon, all of N.J.

[73] Assignee: Pharmacaps, Inc., Elizabeth, N.J.

[21] Appl. No.: 688,748

[22] Filed: Jan. 2, 1985

[51] Int. Cl.$^4$ ............................................ C11D 17/08
[52] U.S. Cl. .................................... 252/93; 252/92; 252/117; 252/118; 252/174; 252/174.13; 252/544; 252/545; 252/DIG. 5
[58] Field of Search ................... 252/92, 93, 117, 118, 252/544, 545, 174, 174.13, 174.14, 174.21, DIG. 5

[56] References Cited

U.S. PATENT DOCUMENTS

| | | | |
|---|---|---|---|
| 2,990,334 | 6/1961 | Graham | 252/DIG. 5 |
| 3,549,544 | 12/1970 | Johnson | 252/545 |
| 4,092,272 | 5/1978 | Nishimura et al. | 252/545 |
| 4,306,997 | 12/1981 | Oneto et al. | 252/545 |
| 4,371,548 | 2/1983 | Hermann et al. | 252/DIG. 13 |

*Primary Examiner*—Paul Lieberman
*Assistant Examiner*—Hoa Van Le
*Attorney, Agent, or Firm*—Merchant, Gould, Smith, Edell, Welter & Schmidt

[57] ABSTRACT

Cosmetic unit dosage forms comprising encapsulated liquid blends of acidic and basic surfactants are provided. The blends are both high-foaming bath compositions and compatible with soft gelatin capsules.

10 Claims, No Drawings

ENCAPSULATED FOAMING BATH COMPOSITION

BACKGROUND OF THE INVENTION

Bathing compositions which foam upon exposure to warm water have found wide consumer acceptance due to the enhanced cleaning power of the foam produced and the cosmetic aspects such as appearance, fragrance and emollience which can be imparted by the ingredients commonly incorporated therein. Liquid bathing compositions, or "bath oils," are available as aqueous solutions or dispersions of mineral oil, wheat germ oil, thickeners, fragrance and the like, which are formulated to incorporate an effective amount of one or more foam-producing surfactants.

Although such liquid compositions can function effectively to foam bath water, their general availability in bulk (bottled) form poses a number of problems. In the first place, the appropriate amount must be pre-measured and poured into the bath water stream, a step which often results in waste or spillage. In the second place, bottled bath oils are bulky and inconvenient to transport. Although the large excesses of water employed to formulate the compositions promote their dispersion in the bath water, the water also increases the shipping weight and storage space required for liquid bath oil compositions.

Soft gelatin encapsulation of a liquid foaming bath oil composition could remedy these deficiencies, providing easily-transportable "unit doses" of the composition in concentrated form. Soft, elastic (SEG) gelatin capsules are stable for long periods under ambient conditions while rupturing readily when exposed to warm water. However, soft gelatin, i.e. of type A or B, is chemically destabilized by alkaline salts, leading to the leaking or bleeding of the capsule contents at elevated pH. This property has heretofore prevented the soft gelatin encapsulation of bath oil compositions such as those which include commonly-used foaming surfactants such as the fatty acid (diethanol)amides. These surfactants exhibit pH's of greater than about 8.0–8.5 as measured in aqueous solution.

Therefore a need exists for a concentrated, high-foaming bath composition which is suitable for, and compatible with, a soft gelatin shell.

BRIEF DESCRIPTION OF THE INVENTION

The present invention provides a cosmetic unit dosage form comprising a soft gelatin capsule containing a liquid, foam-producing blend incorporating a fragrance and a surfactant system. The surfactant system will include a fatty acid (diethanol)amide, the diethanolamine salt of a fatty alcohol(ethylenoxy)sulfate and a fatty alcohol(ethylonoxy)acetic acid. Although the diethanol amide and diethanol amine sulfate surfactants are basic (alkaline), it has unexpectedly been found that the combination of these two surfactants with a fatty alcohol(ethylenoxy)acetic acid surfactant is both high-foaming and compatible (non-reactive) with soft gelatin. Although the mechanism of the interaction of the surfactants is not known, the acidic surfactant is able to counteract the expected degradation of the capsule wall by the basic surfactants without substantially reducing the foaming power of the individual surfactants.

The liquid blend may contain minor amounts of adjuvants such as co-solvents and emollient oils but is otherwise substantially water-free. As used herein, the term "substantially water-free" is defined to mean that water present in the starting materials as provided by the manufacturers or as acquired by hygroscopic attraction may be present in the carrier mixture, as well as minor amounts of added water which are insufficient to deleteriously effect the capsule wall stability.

The common chemical names of the surfactants are in accord with the nomenclature system of the CTFA Cosmetic Ingredient Dictionary (3rd Ed., 1982).

The terms "foam-producing" and "foamable" are intended to indicate the capacity for producing a foam layer upon contact with a warm aqueous medium such as bath water.

DETAILED DESCRIPTION OF THE INVENTION

The compositions of the present invention permit the encapsulation, storage and delivery via soft gelatin encapsulation of basic foamable surfactants which would normally be chemically-incompatible with soft gelatin if incorporated therein in a cosmetically acceptable amount. To overcome this incompatibility, the basic surfactants are combined with an amount of a foamable acidic surfactant effective to render the basic surfactants compatible with flexible, soft gelatin capsules while maintaining the foam-producing ability of the surfactants in aqueous media substantially intact.

The basic, or high pH, surfactants useful in the present foamable surfactant blend are selected from two classes: the diethanol amine salts of fatty alcohol(ethylenoxy)sulfates and the diethanolamides of fatty acids.

Useful sulfate salts include those of the general formula: higher $(C_8-C_{22})alkyl(OCH_2CH_2)_nOSO_3H \cdot HN(CH_2CH_2OH)_2$ wherein n is about 1–5. Commercially-available surfactants of this type include DEA-Laureth Sulfate (available in combination with Cocamide DEA as Monamine ® 779 from Mona Industries, Inc., Paterson, N.J.) and DEA-Myreth Surfate (available in combination with Cocamide DEA as Standapol ® Conc. 7023 from Henkel, Inc.). The commercially-available preparations of these sulfate amine salts are viscous liquids which exhibit pH's of about 8.5–9.0 in 10% aqueous solution.

The high pH surfactants employed in the present surfactant systems will also include at least one (diethanol) amide of a saturated or unsaturated fatty acid of the general formula: higher$(C_8-C_{22})alkylC(=O)N(CH_2CH_2OH)_2$. Useful amide surfactants of this class include lauramide DEA (Monamid ® 716, Mona Industries), cocamide DEA, linoleamide DEA and oleamide DEA. These amides are generally viscous liquids which exhibit pH'of about 9.5–11.0 in 10% aqueous solutions.

The acidic, or low pH, surfactants employed to prepare the present surfactant blends are selected from fatty alcohol(polyethylenoxy)acetic acids of the general formula higher$(C_8-C_{22})alkyl(OCH_2CH_2)_mOCH_2CO_2H$ wherein m is about 3–15, preferably about 5–12. Commercially-available members of this class include trideseth-7-carboxylic acid (Sandopan ® DTC-Acid, Sandoz Chemical Co., East Hanover, N.J.; $C_{13}$-alkyl, m=6) and isosteareth-6-carboxylic acid; $C_{18}$-i-alkyl, m=3; Sandopan ® TA-10. These surfactants are generally oily liquids which exhibit pH's of about 3–4 in 1% aqueous solutions.

Preferably the acidic surfactant will be blended with the basic surfactants in a weight ratio of about 0.5–1.5:1, most preferably about 1:1. The basic surfactant will include at least one member of both the sulfate amine salt and the fatty acid amide. Preferably, one or more of the fatty acid amides will form the major proportion of the basic surfactant blend, most preferably at least about 60% (e.g., 60–80%) of the amide will be present.

The liquid blend of the present invention can also include a minor amount of a $C_2$–$C_4$ diol or triol, preferably propylene glycol and/or glycerin, which can function to adjust the viscosity of the surfactant blend and enhance its release from the ruptured capsule.

Minor but effective amounts of an odoriferous agent selected so as to be chemically-compatible with soft gelatin and the above-described surfactants will be included in the liquid blend. Useful fragrances will include, for instance about 0.5–10%, preferably about 1–5% of floral oils such as rose oil, lavender, lilac, jasmine, wisteria, citrus, apple blossom, or compound bouquets such as spice, pine, woody, oriental, and the like.

Minor amounts of other foam-compatible adjuvants, such as dyes, emollient oils, biocides (preservatives and/or disinfectants) and the like, may be introduced into the present product in effective amounts either via the liquid filler or gelatin wall. When employed in the present products, such adjuvants can be present at levels of up to about 5–10% by weight of the finished product.

Therefore preferred liquid foam-producing blends prepared according to the present invention will comprise about 30–60%, preferably about 40–55% by weight of a basic surfactant comprising a diethanol amine salt of a fatty alcohol(ethylenoxy)sulfate and a diethanolamide of a fatty acid; about 30–60%, preferably about 40–55% of an acidic surfactant comprising a fatty alcohol (polyethylenoxy)acetic acid, about 1–10% fragrance and about 1–10% propylene glycol, preferably about 2–5%.

The liquid foamable blends are generally prepared by mixing together the surfactants under ambient conditions, followed by room temperature addition of the fragrance and the propylene glycol. The resultant blend is mixed until homogeneous and then filled into soft gelatin capsules in a suitable cosmetic unit dose size, e.g. 3000–4000 mg, via a rotary die encapsulation machine or similar encapsulating device.

The invention will be further described by reference to the following detailed example.

EXAMPLE

Lauramide DEA (Monamid ® 716, 5.0 kg), a mixture of DEA Laureth Sulfate and Cocamide DEA (Monamine ® 779, 3.2 kg) and Tridesceth-7-Carboxylic Acid (Sandopan ® DTC-acid 8.2 kg) were blended to homogeneity in a stainless steel mixing vat equipped with mechanical stirring. Citrus-jasmine fragrance (0.52 kg) and propylene glycol (0.5 kg) were added and the viscous liquid stirred an additional 1.0 hour at 25° C. The mixture was filled into spherical soft gelatin (SEG 90 minim) capsules at a dose of 3500 mg per capsule by means of a rotary die encapsulation apparatus. The batch resulted in about $5 \times 10^3$ filled capsules.

Preliminary stability testing indicated that the filled capsules did not leak or bleed after 1–2 months at 37° C. The filled capsules are expected to be indefinitely stable upon storage at controlled room temperatures of 56°–86° F. (15°–30° C.).

When three capsules were contacted with a stream of warm (110°–120° F.) soft city water, the capsule shells ruptured in less than 1 minute and the shell completely dissolved in about 10 minutes. Foaming was evident as soon as the shell opened and the foam layer persisted for about 30 minutes.

Therefore, the Example demonstrates the preparation of a foaming bath oil composition which is quickly released from the capsule upon exposure to warm water, but which does not negatively affect capsule wall stability upon storage.

While certain representative embodiments of the invention have been described herein for purposes of illustration, it will be apparent to those skilled in the art that modifications therein may be made without departing from the spirit and scope of the invention.

What is claimed is:

1. A cosmetic unit dosage form comprising a soft gelatin capsule containing a substantially water-free, liquid blend consisting essentially of:
    (a) from about 0.5% to about 10% of a fragrance;
    (b) from about 30% to about 60% a foamable mixture of basic surfactants comprising a (diethanol)amine salt of a fatty alcohol (ethylenoxy)sulfate and a fatty acid (diethanol)-amide; and
    (c) from about 30% to about 60% an amount of a foamable acidic surfactant comprising fatty alcohol(polyethylenoxy)acetic acid effective to render the liquid blend substantially non-reactive with said gelatin capsule while maintaining the foam-producing ability of the surfactants in aqueous media, said percentages being percentages by weight based on the total weight of the composition, said composition containing not more than 10% by weight of other components.

2. The cosmetic unit dosage form of claim 1 wherein the liquid blend further comprises a $C_2$–$C_5$-diol or triol.

3. The cosmetic unit dosage form of claim 1 wherein the (diethanol)amine salt of a fatty acid(ethylenoxy)sulfate is of the formual:

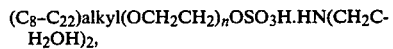
$(C_8\text{–}C_{22})\text{alkyl}(OCH_2CH_2)_nOSO_3H \cdot HN(CH_2CH_2OH)_2$, wherein n is about 1–5, and the fatty acid(diethanol)amide is of the formula:

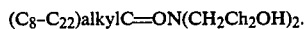
$(C_8\text{–}C_{22})\text{alkylC}=ON(CH_2Ch_2OH)_2$.

4. The cosmetic unit dosage form of claim 1 wherein the fatty alcohol(polyethylenoxy)acetic acid is of the formula:

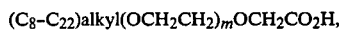
$(C_8\text{–}C_{22})\text{alkyl}(OCH_2CH_2)_mOCH_2CO_2H$, wherein m is about 3–15.

5. The cosmetic unit dosage form of claim 2 wherein the $C_2$–$C_5$-diol comprises propylene glycol.

6. A cosmetic unit dosage form comprising a soft gelatin capsule containing a substantially water-free liquid blend consisting essentially of:
    (a) about 0.5–10% fragrance;
    (b) about 30–60% of a foamable mixture of basic surfactants comprising a fatty acid (diethanol)-amide and a basic surfactant of the formula:

$(C_8-C_{22})alkyl(OCH_2CH_2)_nOSO_3H \cdot HN(CH_2CH_2OH)_2,$ wherein n is about 1–5;

(c) about 30–60% of a foamable acidic surfactant comprising a surfactant of the general formula:

$(C_8-C_{22})alkyl(OCH_2CH_2)_mOCH_2CO_2H,$ wherein m is about 3–15; and (d) about 2–5% propylene glycol said percentages being percentages by weight based on the total weight of the composition, said composition containing not more than 10% by weight of other components.

7. The cosmetic unit dosage form of claim 6 wherein the foamable acidic surfactant comprises tridesceth-7-carboxylic acid.

8. The cosmetic unit dosage form of claim 6 wherein the weight ratio of the acidic surfactant to the basic surfactant mixture is about 0.5–1.5:1.

9. The cosmetic unit dosage form of claim 6 wherein about 3000–4000 mg of the liquid blend is contained by said gelatin capsule.

10. The cosmetic unit dosage form of claim 8 wherein the fatty acid (diethanol)amide comprises at least 60% of the mixture of basic surfactants.

* * * * *

UNITED STATES PATENT AND TRADEMARK OFFICE
CERTIFICATE OF CORRECTION

PATENT NO. : 4,597,885
DATED : July 1, 1986
INVENTOR(S) : Ira R. Berry et al.

It is certified that error appears in the above-identified patent and that said Letters Patent is hereby corrected as shown below:

At Column 2, line 55, for "pH' of" read --pH's of--.

At Column 4, line 43, for "formual:" read --formula:--.

At Column 4, line 50, for

"$(C_8-C_{22})alkylC=ON(CH_2Ch_2OH)_2$" read

--$(C_8-C_{22})alkylC=ON(CH_2CH_2OH)_2$--.

Signed and Sealed this

Twenty-third Day of September 1986

[SEAL]

Attest:

DONALD J. QUIGG

Attesting Officer

Commissioner of Patents and Trademarks